US005777138A

United States Patent [19]

Bannister et al.

[11] Patent Number: 5,777,138
[45] Date of Patent: Jul. 7, 1998

[54] RING-OPENING AMIDATION PROCESS

[75] Inventors: Robin Mark Bannister; Neil Henderson; Graham Ruecroft, all of Cambridge, United Kingdom

[73] Assignee: Chriroscience Limited, Cambridge, United Kingdom

[21] Appl. No.: 793,617

[22] PCT Filed: Sep. 12, 1995

[86] PCT No.: PCT/GB95/02183

§ 371 Date: Mar. 12, 1997

§ 102(e) Date: Mar. 12, 1997

[87] PCT Pub. No.: WO96/08465

PCT Pub. Date: Mar. 21, 1996

[30] Foreign Application Priority Data

Sep. 12, 1994 [GB] United Kingdom ............... 9418357

[51] Int. Cl.$^6$ .......................................... C07D 317/44

[52] U.S. Cl. ........................ 549/436; 548/431; 564/189

[58] Field of Search ........................ 549/436; 548/431; 564/189

[56] References Cited

PUBLICATIONS

J. Chen et al., A Novel and Efficient Route to Chiral 2-Substituted Carbocyclic 5'-N-Ethyl-Carboxamido-Adenosine (C-NECA), Tetrahedron Letters, vol. 30, No. 41, 1989, pp. 5543–5546.

Primary Examiner—Richard L. Raymond
Attorney, Agent, or Firm—Foley & Lardner

[57] ABSTRACT

A process for amidating a 2-azabicyclo[2.2.1]heptan-3-one or a 2-azabicyclo[2.2.1]hept-5-en-3-one by reaction with an amine, to form the corresponding ring-opened amide, is modified by the addition of an additive that accelerates the rate of reaction to an extent that the reaction can be carried out at atmospheric pressure.

13 Claims, No Drawings

RING-OPENING AMIDATION PROCESS

FIELD OF THE INVENTION

This is a National stage application pursuant to 35 USC § 371 of PCT/GB95/02183, filed Sep. 12, 1995.

This invention relates to a ring-opening amidation process, e.g. to prepare the ring-opened amide [3aR,4S,6R,6aS]-6-amino-N-ethyltetrahydro-2,2-dimethyl-4H-cyclopenta-1,3-dioxole-4-carboxamide (formula 2) which is a chiral building block en route to compounds with potent activity on the adenosine $A_2$ receptor (vasodilators).

BACKGROUND OF THE INVENTION

Chen et al. Tet. Lett. 30(41):5543 (1989), disclose amidation of the racemic lactam tetrahydro-2,2-dimethyl-4,7-methano-1,3-dioxolo[4,5C]pyridin-6(3aH)-one (formula 1) by ethylamine to give the ring-opened amide (2); see Scheme 1. The reaction is carried out in neat ethylamine. Since an appreciable reaction rate is observed only above about 100° C., the reaction must be carried out under pressure, e.g. 1,500 kPa at 120° C., owing to the volatility of the ethylamine. The resulting requirement for specialised reactors makes this process uneconomic, on a manufacturing scale.

SUMMARY OF THE INVENTION

The present invention is based upon the surprising discovery that the rate of amidation can be increased to the extent that it can be conducted at atmospheric pressure. Thus, the reaction of Scheme 1 can be conducted in the presence of ethylammonium ion. For example, ethylammonium chloride at 1 mol % was found to enhance the rate of ethylamine ring-opening (see Scheme 1) by 5-fold, relative to typical non-catalysed conditions of 12 h at 120° C., 1,500 kPa.

This invention will be described with reference to the Schemes below, reactants of formula (1) and ethylamine, but this by way of example only. Any suitably protected lactam, and ammonia or any suitable primary or secondary amine can be used. For example, the amine may have the formula $R_1R_2NH$, wherein $R_1$ and $R_2$ are independently selected from H or alkyl, or aryl e.g. aryl, or any other non-interfering substituent. In this case, if acid is used, the reaction may be conducted in the presence of $R_1R_2NH_2^+X^-$ wherein $X^-$ is a suitable counteranion.

Further, the invention is not limited to the use of the particular acetonide shown in the formulae, below. Any readily-removable OH blocking group (acetonide-type) or groups may be used. The invention is thus applicable to the amidation of any compound having the 2-a2abicyclo[2,2,1] heptan-3-one structural nucleus. The compound may be saturated or unsaturated, substituted or unsubstituted, in racemic or, preferably, substantially enantiopure form. In particular, the invention relates to the amidation of any tetrahydro-2,2-dialkyl-4,7-methano-1,3-dioxolo[4,5-C] pyridin-6(3aH)-one.

DESCRIPTION OF THE INVENTION

Product (2) can be converted to its benzoic acid salt (3) by reaction with benzoic acid in tetrahydrofuran. This benzoate salt, being of crystalline nature, at least for the pure enantiomer, is a convenient form for isolation of the pure product.

Nevertheless, a preferred aspect of this invention is based upon the surprising discovery that, when 1 mol equivalent of ethylammonium benzoate is present in addition to 2 mol equivalents of anhydrous ethylamine, the reaction progresses cleanly and conveniently to the salt (3) according to Scheme 2. Thus, all the ethylammonium benzoate is consumed at the point of complete reaction.

Free ethylamine may be used in catalytic (5 mol %) amounts only and ethylammonium benzoate provides the stoichiometric source of ethylamine. Although significantly slower compared with 2 mol equivalents of ethylamine, 80% reaction is achieved in 24 h in tetrahydrofuran (THF) under conditions of reflux.

In another preferred aspect of the invention, the reaction is conducted in a solvent. It has been discovered that the amidation to prepare (2) can be carried out at reflux using 70% aqueous ethylamine, using as co-solvent tetrahydrofuran, propan-2-ol or butan-1-ol. This represents an advantageous process over the prior art since high pressures and temperatures are circumvented, thus avoiding the need for costly pressure apparatus.

A further advantage is the use of cheaper, more easily handled aqueous ethylamine as opposed to pure anhydrous amine, as described by Chen et al, supra. A disadvantage of using aqueous ethylamine is that over the reaction, partial hydrolysis to form the amino-acid (4) may be evident. This hydrolysis is avoided if anhydrous ethylamine is used in the appropriate co-solvent. Once again, ethylammonium ion considerably enhances the rate of amidation at atmospheric pressure.

In summary, the present invention provides a much simplified process, circumventing high pressure amidation, high excesses of anhydrous ethylamine, multi-step chemistry and costly processing.

The following Examples 1 and 2 illustrate the invention, with respect to the Comparative Example.

COMPARATIVE EXAMPLE

The protected diol single-enantiomer (1, 475 g, 2.54 mol) was dissolved in pre-distilled anhydrous ethylamine (1.25 l) containing ethylammonium chloride (1.2 g, 26.6 mmol). The solution was heated to 120° C. under pressure (1,500 kPa) for 3.5 h. Following cooling to 20° C., the ethylamine was removed under vacuum.

To the residual viscous crude amide (2, 580 g) was added THF (1.3 l). Benzoic acid (310 g, 2.54 mol) was dissolved in THF (1.2 l). This solution was added over 0.5 30 h to the stirring amide solution at 25° C. The crop was filtered, washed with THF (0.3 l) and recrystallised from THF containing 18% ethanol (2.9 l). The yield was 600 g (67%) from 800 g of crude salt (90%).

Example 1

The protected diol (2, 10.3 g, 52.5 mmol) was dissolved in butan-1-ol (50 ml). To this solution was added 70% ethylamine in water (30 ml) followed by ethylammonium chloride (2.0 g, 4.4 mmol). The mixture was brought to reflux (76° C.) for 15 h. The solution was concentrated under vacuum and residual water removed by azeotropic distillation with toluene (30 ml).

The yield of crude product was 15.5 g which was dissolved in THF (50 ml). The benzoic acid salt was formed as in the Comparative Example using benzoic acid (6.4 g, 52.5 mmol). The yield of crude salt was 14.2 g (72%).

Example 2

The protected diol (2, 91.5 g, 0.5 mol) was suspended in THF. Ethylamine (100 ml, 1.53 mol) was added with stirring at 5° C. Benzoic acid (61 g, 0.5 mol) in THF (100 ml) was added at this temperature over 30 min. The solution was brought to reflux for 18 h (internal temperature 55°–60° C.). The solution was concentrated under vacuum until precipitation occurred. After cooling to 10° C., the salt was filtered and washed with THF (50 ml). The liquors were concentrated to produce a second crop. The total yield was 140 g (80%) which was recrystallised from THF/18% ethanol (300 ml). The yield was 115 g (65%) first crop and 9 g (5%) second crop. Total 124 g (70%).

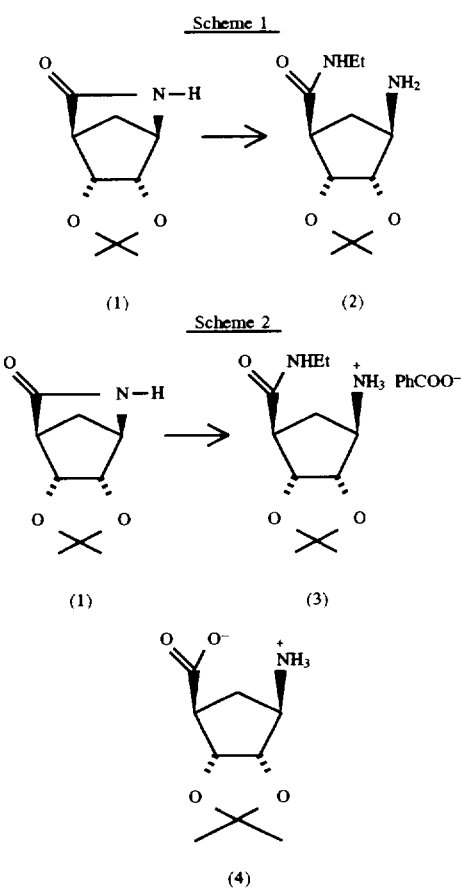

We claim:

1. A process for preparing a cis-1-amino-3-carboxyamidocyclopentane or a cis-1-amino-3-carboxyamidocyclopent-4-ene, comprising reacting a 2-azabicyclo[2.2.1]heptan-3-one or a 2-azabicyclo[2.2.1]hept-5-en-3-one with an acid salt of an amine at atmospheric pressure.

2. The process according to claim 1, further comprising reacting said 2-azabicyclo[2.2.1]heptan-3-one or said 2-azabicyclo[2.2.1]hept-5-en-3-one with said salt in the presence of a solvent.

3. The process according to claim 2, wherein said solvent comprises at least one solvent selected from the group consisting of water, tetrahydrofuran, propan-2-ol, and butan-1-ol.

4. The process according to claim 1, wherein said acid salt is a hydrochloride or benzoate salt.

5. The process according to claim 1, wherein said amine has the structure $R^1R^2NH$, wherein $R^1$ and $R^2$ independently are selected from the group consisting of H, alkyl, and aryl.

6. The process according to claim 5, wherein said amine is ethylamine.

7. The process according to claim 1, wherein said 2-azabicyclo[2.2.1]heptan-3-one is a tetrahydro-2,2-dialkyl-4,7-methano-1,3-dioxolo[4,5-C]pyridin-6(3aH)-one.

8. The process according to claim 1, wherein said 2-azabicyclo[2.2.1]heptan-3-one or said 2-azabicyclo[2.2.1]hept-5-en-3-one is substantially enantiomerically pure.

9. The process according to claim 7, wherein said tetrahydro-2,2-dialkyl-4,7-methano-1,3-dioxolo[4,5-C]pyridin-6(3aH)-one is tetrahydro-2,2-dimethyl-4,7-methano-1,3-dioxolo[4,5-C]pyridin-6(3aH)-one.

10. The process according to claim 2, wherein said reaction is carried out under reflux.

11. The process according to claim 1, wherein the free amine also is present.

12. The process according to claim 1, where the reaction is carried out in the absence of water.

13. The process according to claim 3, where the reaction is carried out in the presence of water.

* * * * *